United States Patent
De Ferra et al.

(10) Patent No.: US 9,266,863 B2
(45) Date of Patent: Feb. 23, 2016

(54) PROCESS FOR THE SYNTHESIS OF AZACITIDINE AND DECITABINE

(75) Inventors: Lorenzo De Ferra, Patrica (IT); Maurizio Zenoni, Patrica (IT); Stefano Turchetta, Patrica (IT); Mauro Anibaldi, Patrica (IT); Ettore Ammirati, Patrica (IT); Paolo Brandi, Patrica (IT); Giorgio Berardi, Patrica (IT)

(73) Assignee: CHEMI SPA, Cinisello Balsamo (MI) (IT)

( * ) Notice: Subject to any disclaimer, the term of this patent is extended or adjusted under 35 U.S.C. 154(b) by 281 days.

(21) Appl. No.: 13/073,014

(22) Filed: Mar. 28, 2011

(65) Prior Publication Data

US 2011/0245485 A1      Oct. 6, 2011

(30) Foreign Application Priority Data

Mar. 30, 2010   (IT) .............. MI2010A0524

(51) Int. Cl.
  *C07H 19/12* (2006.01)
  *C07H 1/00* (2006.01)
  *C07D 405/04* (2006.01)
(52) U.S. Cl.
  CPC ............ *C07D 405/04* (2013.01); *C07H 1/00* (2013.01); *C07H 19/12* (2013.01)

(58) Field of Classification Search
  None
  See application file for complete search history.

(56) References Cited

U.S. PATENT DOCUMENTS 7,038,038 B2 * 5/2006 Ionescu et al. .............. 536/28.3
2010/0036112 A1   2/2010 Henschke et al.

FOREIGN PATENT DOCUMENTS

EP         2050757 A1 *  4/2009  ............. C07H 19/12

OTHER PUBLICATIONS

Klebe, J. F. et al., Journal of the American Chemical Society, "Silylations with Bis(trimethylsilyl) acetamide a Highly Reactive Silyl Donor", vol. 88, No. 14, pp. 3390-3395.*
Sigma Aldrich, "BSTFA Product Specification", published 1997.*

* cited by examiner

*Primary Examiner* — Shaojia Anna Jiang
*Assistant Examiner* — Bahar Craigo
(74) *Attorney, Agent, or Firm* — Silvia Salvadori, P.C.; Silvia Salvadori

(57) ABSTRACT

Described herein is a process for the synthesis of azacitidine or decitabine, comprising the silylation of azacytosine in the presence of N,O-bis-trimethylsilyl-trifluoroacetamide. Such reaction is performed in an organic solvent, preferably aprotic, even more preferably selected from among dichloromethane, dichloroethane and/or acetonitrile. According to a further aspect of the process, 2 to 3 moles of N,O-bis-trimethylsilyl-trifluoroacetamide are used per mole of azacytosine, preferably from 2.2 to 2.5.

17 Claims, No Drawings

PROCESS FOR THE SYNTHESIS OF AZACITIDINE AND DECITABINE

RELATED APPLICATIONS

This application claims priority to and benefit from Italian Application No. MI2010A000524 filed on Mar. 30, 2010, the content of which is incorporated herein by reference.

FIELD OF THE INVENTION

The invention relates to the synthesis of azacitidine (also referred to as amino-1-β-D-ribofuranosyl-1,3,5-triazin-2(1H)-one) and decitabine (also referred to as 4-amino-1-(2-deoxy-β-D-ribofuranosyl-1,3,5-triazin-2(1H)-one).

PRIOR ART IN THE FIELD OF THE INVENTION

Various drugs with a chemical structure analogous to that of natural nucleosides are used in the field of antiviral and antitumor drugs.

Azacitidine, whose structural formula is indicated below,

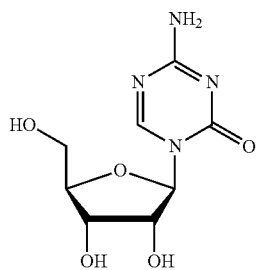

AZACITIDINE 1 is an antitumor drug effective for the treatment of the Myelodysplastic Syndrome (MDS) and it was the first drug approved by the FDA for this disease.

The synthesis thereof, based on the construction of the s-triazine ring starting from a conveniently substituted sugar, was reported for the first time in Collect. Czech. Chem. Commun. 29, 2060 (1964) and it also was reported in U.S. Pat. No. 3,350,388. Synthetic schemes which provide for the silylation of azacytosine, whose structural formula is indicated below,

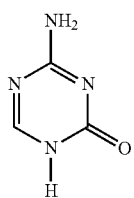

AZACYTOSINE 2 and the subsequent coupling with ribose derivatives, allow to prepare Azacitidine with a lower number of steps.

A derivative of D-ribose with an acyloxy group in position 2 which determines, according to Baker's rule, a good selectivity in favour of the isomer β in the coupling reaction, according to the synthesis scheme indicated below, is usually employed.

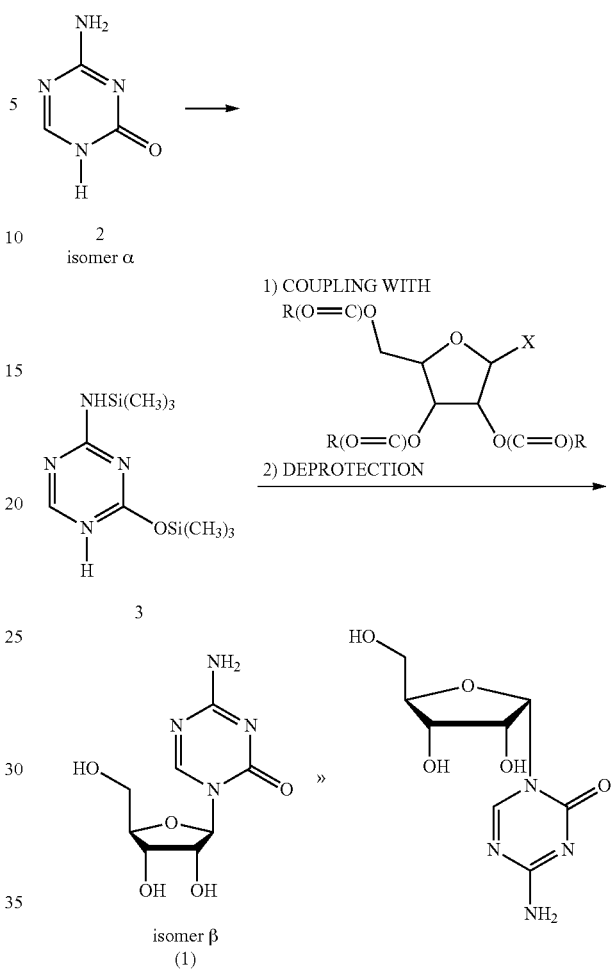

Various experimental procedures following this synthetic approach are indicated in the scientific and patent literature.

The synthesis of azacitidine by reacting silylated azacytosine 3 with tri-O-acetyl-D-ribofuranosyl bromide is described in J. Org. Chem. 35, 491 (1970). The indicated yield is equal to 34% which is reduced to 11% after crystallisation. Such yields, in combination with the use of a reagent difficult to handle like the bromide derivative of ribose, makes such procedure unsuitable for preparing azacitidine at commercial scale.

Vorbrüggen and Niedballa in J. Org. Chem. 39, 3672 (1974) and U.S. Pat. No. 3,817,980 describe a process for the preparation of protected azacitidine with a yield of 81%. The article does not indicate the yield after deprotection. The process provides for the silylation of azacytosine with a mixture of hexamethyldisilazane (HMDS) and trimethylsilyl chloride (TMSCl) in pyridine. At the end of the reaction the excess of the reagents and pyridine are removed to avoid inactivation of the coupling catalyst (see Vorbrüggen and Niedballa J. Org. Chem. 39, 3654 (1974)).

This operation is performed by means of distillation under vacuum until a liquid which crystallises is obtained and which is washed with benzene.

Considering the difficulties encountered when treating and stirring a distillation residue which solidifies and the problems related to the use of solvents harmful to health such as benzene, it is clear how such operations may exclusively find application in a small scale laboratory preparation.

Another drawback observed following this procedure, which provides for the use of tin tetrachloride as coupling catalyst, lies in the fact that it is difficult to keep the level of residue tin in the final azacitidine at acceptable levels.

A contribution to the solution of these problems of synthesis of azacitidine is indicated in the article of Piskala and Sorm (Nucleic Acid Chemistry 435 (1978)): in this case, toluene, which is a less toxic solvent, is used when purifying the silylated azacytosine instead of benzene. Furthermore, the authors use tri-O-benzoyl-D-ribofuranosyl chloride in acetonitrile, without adding catalysts, for the subsequent coupling reaction. However, there still remains the difficulty represented by the removal of hexamethyldisilazane (HMDS) used in excess in the silylation reaction, performed even in this case until a residue which solidifies is obtained and additionally, by the work up of the coupling reaction, in which the use of a laboratory spatula for disintegrating the reaction mixture into small pieces is provided for. Clearly, such processes are not scalable in the production of azacitidine for pharmaceutical use.

U.S. Pat. No. 7,038,038 described the following process: tetraacetyl-D-ribose (4) is reacted with the silylated azacytosine (3), in turn obtained by reacting (two hours) azacytosine with hexamethyldisilazane (HMDS) in the presence of ammonium sulfate under heat (see the synthesis scheme indicated below).

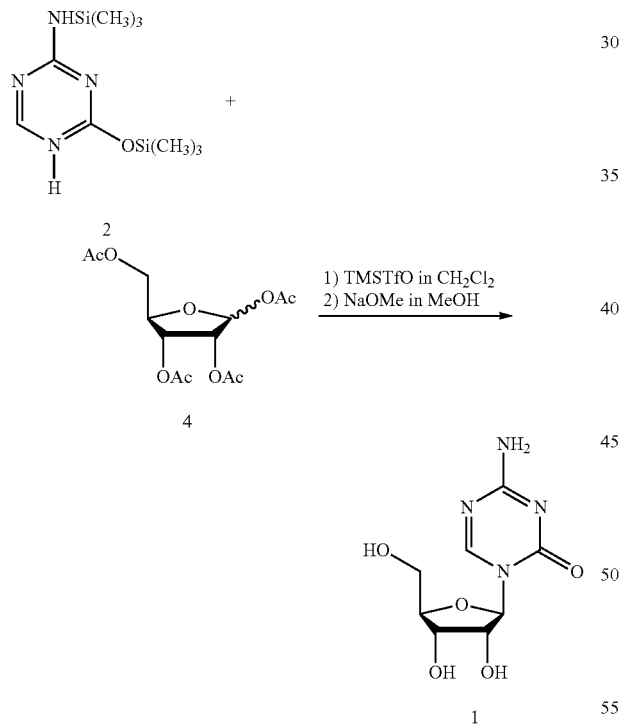

Before coupling with tetraacetyl ribose, the excess of silylating agent is removed by distillation to residue. The coupling reaction occurs in dichloromethane, provides for the use of trimethylsilyltriflate (TMSOTf) as catalyst and has a duration of two hours. Lastly, the removal of acetyl groups occurs by reacting with sodium methylate in methanol. Such method allows the production of Azacitidine with yield of 44.9%, but it is also not suitable for production of azacitidine at commercial scale due to the need of removing the excess of HMDS until a pasty mixture, which is difficult to stir, is obtained. An attempt to solve such problem may be found in the same document (U.S. Pat. No. 7,038,038) as indicated in examples 5 and 6: the silylation reaction is performed with a mixture of reagents (HMDS and Trimethylsilyl chloride) in acetonitrile; to the reaction mixture containing the silylated nucleobase, TMSOTf as a coupling catalyst and tetraacetyl derivative of ribose, are added to obtain protected azacytosine. Though representing a simplification of the synthesis, such process leads to an increase of the duration of the reactions (twenty hours both for silylation and coupling) and to lowering the yield which is equal to 41.3% for a raw product, whose purity or yield of transformation into azacitidine of the pharmaceutical level required for use thereof as an active ingredient for human use, are not indicated.

The nucleobase azacytosine 2 is used as a starting material even for the synthesis of another drug, decitabine 5, whose main indication is Myelodysplastic Syndrome (MDS).

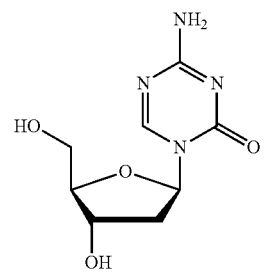

DECITABINE 5

The problems described regarding the synthesis of azacitidine are also observed in the case of decitabine with a further complication deriving from the fact that the absence of the hydroxyl group in position 2' of decitabine does not allow exploiting the greater selectivity towards the isomer β in the coupling reaction when an acylated hydroxyl group is present in that position (Baker's rule).

The use of the derivative 3 obtained through double-silylation from azacytosine 2 (according to the scheme indicated below) even for the preparation of decitabine, is present in literature.

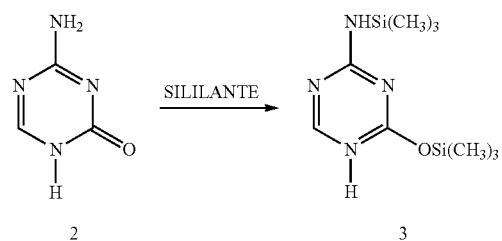

Also in this case, in order to avoid possible interferences in the subsequent steps of the process, all volatile components present at the end of the reaction are removed by distillation (see for example U.S. Pat. No. 3,817,980, EP2048151 and WO2009086687). Such procedure is not suitable for production at industrial level considering that the residue, during concentration, tends to solidify and hence the stirring systems could operate irregularly or be damaged. In the synthesis of decitabine indicated in J. Org. Chem. 51, 3211 (1986) the bis-silylated azacytosine is added to the reaction mixture.

Even this operation, which requires the handling of a substance sensitive to contact with the ambient moisture, is scarcely applicable in production scale.

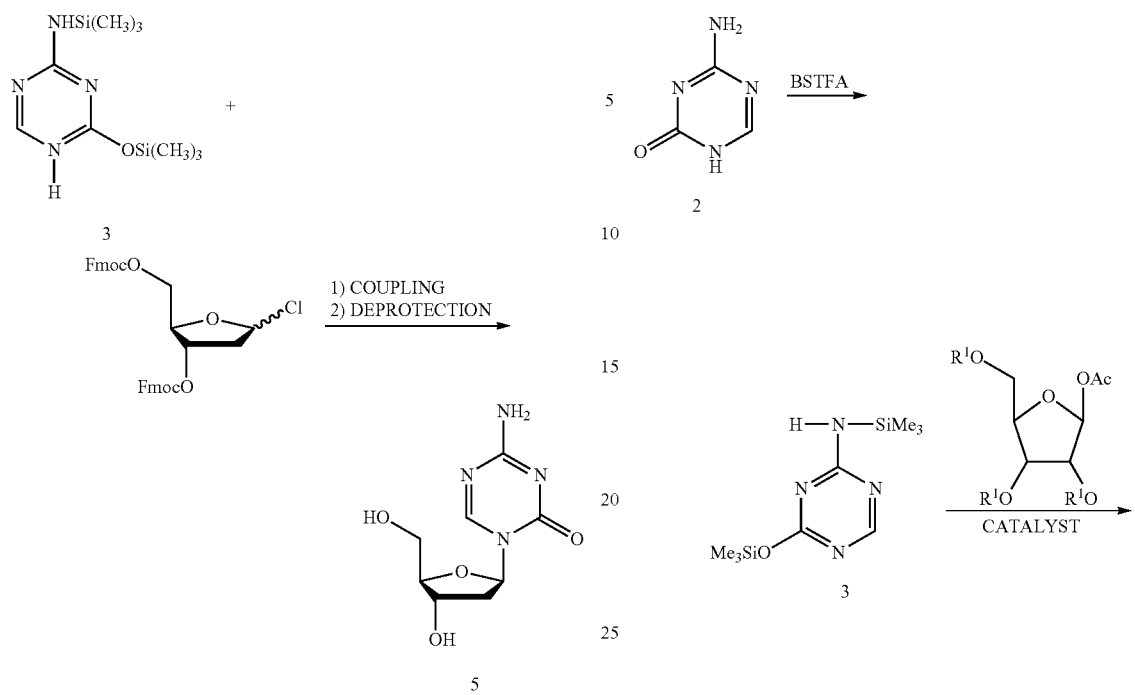

Described in US2010/0036112 is a process for the synthesis of azacitidine, comprising the silylation reaction of azacytosine with hexamethyldisilazane (HMDS), the coupling reaction of the silylated intermediate thus obtained with 1-O-acetyl-2,3,5-tri-O-benzoyl-β-D-ribofuranose in acetonitrile, and the subsequent reaction of deprotection of the product of the coupling reaction to obtain azacitidine. The silylation reaction is directly performed in large molar excess of hexamethyldisilazane, with consequently high production costs; furthermore, the silylated intermediate thus obtained must be isolated before being subjected to the subsequent coupling reaction in acetonitrile, with a further increase of production costs.

It is thus apparent that the processes currently available for the synthesis of nucleosides deriving from azacytosine still reveal unresolved problems related to their possible use at industrial level.

DESCRIPTION OF THE INVENTION

A method for the synthesis of azacitidine and decitabine suitable for commercial production scale able to allow the products to be isolated with good yields and with high purity, without having to use a large molar excess of silylation reagents and the operation of removing the excess of silylation reagents still present at the end of the reaction was found for the first time with the present invention. All the operations of the method subject of the present invention are suitable for the production in commercial scale of azacitidine and decitabine and may be conveniently performed sequentially avoiding the steps of work up and isolation of intermediates with consequent reduction of the duration of the process and improvement of productivity.

The embodiment of the present invention consists in the preparation of azacitidine according to the following scheme.

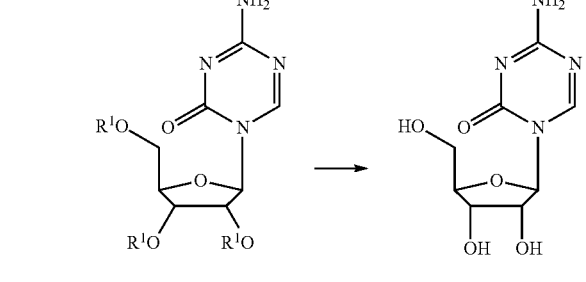

Wherein Ac represents acetyl and $R^1$ is preferably selected from among acetyl and/or benzoyl.

The corresponding scheme for the synthesis of decitabine is as follows.

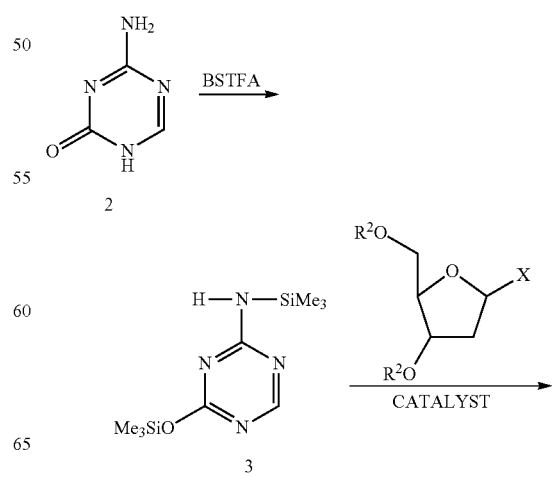

-continued

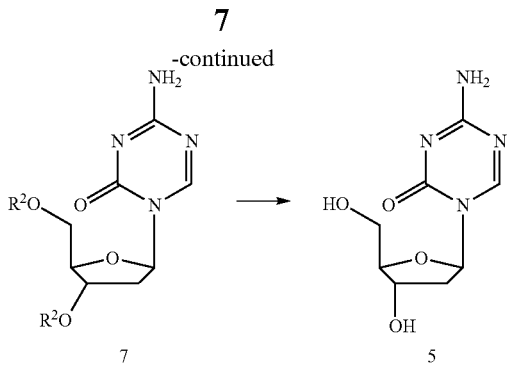

Wherein R² is preferably selected from among acetyl, p-toluoyl, p-chloro-benzoyl and/or p-nitro-benzoyl and X is preferably selected from among an alkoxy group, an acyloxy group or a halogen, preferably a methoxy group, an acetyloxy group or a chlorine atom. It was surprisingly found that, by using N,O-bis-trimethylsilyl-trifluoroacetamide (BSTFA) as a silylating reagent of the nucleobase azacytosine 2, to obtain the silylated azacytosine 3, it is possible to complete the silylation reaction at low temperature and within short periods of time using a low molar excess of BSTFA. In addition, it was found that, without having to replace the solvent and without having to remove the excess of silylating agent or the reaction by-products thereof, it is possible to directly perform the subsequent coupling reaction by simply adding the derivative of sugar and the catalyst to the mixture of the silylation reaction. Even this second reaction proceeds at mild conditions and its completion occurs in few hours.

A distinctive characteristic of the present invention, which entails an advantageous simplification of the production process both of azacitidine and decitabine, lies in the fact that the silylated azacytosine 3 is not isolated.

Furthermore, the final reaction of deprotection may be performed without necessarily having to isolate the protected nucleoside, but by directly alkalinizing using a suitable reagent, such as for example sodium methylate or ammonia, the mixture of the previous coupling reaction after having performed a suitable change of solvent.

Alternatively, still avoiding isolation of protected nucleoside, the conditions described in the prior art, such as for example deprotection using sodium methylate in methanol or ammonia in methanol, after a simple aqueous work up, may be used.

Various organic solvents, preferably aprotic, even more preferably non-silylated, among which dichloromethane, dichloroethane and/or acetonitrile may be used for the silylation reaction and coupling to implement the present method; preferably, dichloromethane and/or acetonitrile is used as solvent. The proportion between the amount of organic solvent and that of the substrates left to react is not a critical parameter of the process and 3 to 100 parts in volume (liters) of organic solvent may be used for each part by weight (kilogram) of azacytosine.

The process subject of the present invention allows to avoid the waste of silylation reagent typical of the procedures currently used; as a matter of fact a slightly higher amount of moles with respect to that provided for the double silylation of azacytosine may be used. Preferably 2 to 3 moles of BSTFA may be used per mole of azacytosine, even more preferably 2.2 to 2.5 are used per mole of azacytosine.

A further particularly useful aspect of this process lies in the fact that the handling of silylated azacytosine, which is a compound unstable upon contact with water and atmospheric moisture, is minimised.

The silylation reaction may be performed at temperatures between 0° and the reflux temperature of the reaction mixture, preferably between 25° C. and said reflux temperature, even more preferably at a temperature below 100° C.

By operating under the reaction conditions of the present method, the silylation reaction of azacytosine is completed in few hours and usually such completion occurs in less than four hours.

Derivatives of D-ribofuranose with the acylated hydroxyl function are used in the coupling reaction for the implementation of the present method for the synthesis of azacitidine. Conveniently useable among these may be 1,2,3,5-tetra-O-acetyl-D-ribofuranose or 1-O-acetyl-2,3,5-tri-O-benzoyl-D-ribofuranose commercial derivatives; more preferably 1,2,3,5-tetra-O-acetyl-D-ribofuranose is used.

Derivatives of D-2-deoxyribofuranose having a leaving group in position 1 and the other acylated hydroxyl functions may be used for the synthesis of decitabine. The leaving group in position 1 may be an alkoxy group, an acyloxy group or a halogen, more preferably it may be a methoxy group, an acetyloxy group or a chlorine, even more preferably chlorine. Among the acyl group, the acetyl group, the p-toluoyl group, the p-chloro-benzoyl group and the p-nitro-benzoyl group may be conveniently used for protecting the other hydroxyl functions of deoxyribose; the p-toluoyl group and the p-chloro-benzoyl group may be preferably used. The commercial products preferably used for the synthesis of decitabine are 1-chloro-3,5-di-p-toluoyl-2-deoxy-D-ribofuranose and 1-chloro-3,5-bis-p-chlorobenzoyl-2-deoxy-D-ribofuranose.

The presence of a Lewis acid catalyst facilitates the coupling reaction. Catalysts usually employed in this type of reaction such as tin tetrachloride, titanium tetrachloride, zinc chloride, boron trifluoride etherate, trimethylsilyltriflate and trimethylsilylnonaflate are preferable. Trimethylsilyltriflate (TMSTfO) is particularly preferred as a catalyst in the coupling reaction.

Even for the coupling reaction, the reaction temperature may be comprised between 0° and the reflux temperature of the reaction mixture, preferably between 25° C. and said reflux temperature, even more preferably below 100° C. In the indicated reaction conditions, the reaction proceeds within a short period of time and it is typically complete within less than four hours both in the case of azacitidine and in the case of decitabine. For both products, at the end of the coupling reaction it is possible to proceed directly to the final reaction of deprotection by simply replacing the reaction solvent used for the coupling with the solvent of the deacylation reaction, which may preferably be a $C_1$-$C_4$ alcohol, preferably methanol.

Such process is extremely practical and particularly advantageous in that it allows to avoid the use of aqueous solutions in the entire synthetic sequence. Such result is particularly significant considering the quick degradation of the triazine ring present in the molecule object of the present invention upon contact with water (see for example J. Med. Chem. 21, 204(1978)).

Alternatively, at the end of the coupling reaction, the reaction mixture may be washed using buffered aqueous solutions following the teachings of literature (for example see J. Org. Chem. 35, 491 (1970), J. Org. Chem. 39, 3672 (1974) and U.S. Pat. No. 7,038,038).

Without having to proceed to the isolation of the intermediate protected nucleoside and purification thereof by chromatography and/or by crystallisation, regardless of the type of work up adopted at the end of the coupling reaction, the synthesis is completed by deprotection in a $C_1$-$C_4$ alcohol, preferably in methanol, with ammonia or sodium methylate, according to the processes previously known in the art (such as for example J. Org. Chem. 35, 491 (1970), J. Org. Chem. 39, 3672 (1974) and U.S. Pat. No. 7,038,038).

In the case of azacitidine, by using methanol as a solvent in the deprotection reaction, its crystallisation directly during the reaction occurs to obtain, with yields exceeding 35% and even exceeding 75%, good quality azacitidine (HPLC purity>90%). A single recrystalisation from DMSO/methanol mixtures leads to azacitidine with HPLC purity≥99.8%.

Even in the case of decitabine, if methanol is used as a solvent in the deprotection reaction, there occurs the crystallisation of the product directly during the reaction to obtain, with yields exceeding 30%, high quality decitabine (HPLC purity>99%). The combination of the simplicity of the process with the high quality of the products obtained and the high process yield makes the present invention particularly advantageous for the preparation of azacitidine and decitabine at commercial scale. The examples that follow have the purpose of illustrating some of the possible embodiments of the present invention and they shall not be intended to be restrictive thereto.

EXAMPLES

Example 1

Preparation of Azacitidine 34.7 mL of BSTFA are added to a suspension of 6.3 g of azacytosine in 126 mL of dichloromethane. The mixture is brought to reflux temperature and it is stirred for 90 minutes. 11.35 mL of trimethylsilyltriflate and then a solution of 16.7 g of 1,2,3,5-tetra-O-acetyl-D-ribofuranose in 33 mL of dichloromethane are added to the limpid solution, in about ten minutes. Reflux and stirring is maintained for two hours, it is cooled to room temperature and it is poured on a solution of 9.5 g of sodium bicarbonate in 330 ml of water. It is stirred for ten minutes, the pH is adjusted to pH=4.5 using acetic acid. It is left to settle, phases are separated, the aqueous phase is washed twice using 125 ml of dichloromethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 10 mL of a 10% solution of sodium methylate in methanol are added. It is stirred for 1 hour, it is cooled to room temperature, it is stirred to complete precipitation and the solid is filtered by washing it on the filter with methanol.

6.5 g of azacitidine with HPLC purity (UV 254 nm) of 93.8% are obtained after drying at low pressure.

Example 2

Preparation of Azacitidine 34.7 mL of BSTFA are added to a suspension of 6.3 g of azacytosine in 126 mL of acetonitrile. The mixture is brought to 50° C. and it is stirred for 90 minutes. 11.35 mL of trimethylsilyltriflate and then a solution of 16.7 g of 1,2,3,5-tetra-O-acetyl-D-ribofuranose in 33 mL of acetonitrile are added to the limpid solution, in about ten minutes. Stirring is maintained for 75 minutes, it is cooled to room temperature and it is slowly poured onto a mixture constituted by 500 ml of dichloromethane and 330 ml of water into which 9.5 g of sodium bicarbonate had been previously dissolved. Stirring is carried out for 15 minutes and the pH is adjusted to pH=4.5 using acetic acid. The mixture is left to settle and phases are separated. The aqueous phase is washed twice using 125 ml of dichloromethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 15 mL of a 10% solution of sodium methylate in methanol are added. It is stirred for 1 hour, it is cooled to room temperature, it is stirred to complete precipitation and the solid is filtered by washing it on the filter with methanol.

8.5 g of azacitidine with HPLC purity (UV 254 nm) of 98.7% are obtained after drying at low pressure.

Example 3

Preparation of Azacitidine 34.7 mL of BSTFA are added to a suspension of 6.3 g of azacytosine in 126 mL of dichloromethane. The mixture is brought to reflux temperature and it is stirred for 90 minutes. 62 mL of a 1M solution of tin tetrachloride in dichloromethane and then a solution of 16.7 g of 1,2,3,5-tetra-O-acetyl-D-ribofuranose in 33 mL of dichloromethane are added to the limpid solution in about ten minutes. Reflux and stirring are maintained for 75 minutes, it is cooled to room temperature and it is poured on a solution of 9.5 g of sodium bicarbonate in 330 ml of water. It is stirred for ten minutes, the pH is adjusted to pH=4.5 using 30% sodium hydroxide in water. It is left to settle, it is filtered on earth filter and phases are separated, the aqueous phase is washed twice using 125 ml of dichloromethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 10 mL of a 10% solution of sodium methylate in methanol are added. It is stirred for 1 hour, it is cooled to room temperature, it is stirred to complete precipitation and the solid is filtered by washing it on the filter with methanol.

5.2 g of azacitidine with HPLC purity (UV 254 nm) of 96.5% are obtained after drying at low pressure.

Example 4

Preparation of Azacitidine 34.7 mL of BSTFA are added to a suspension of 6.3 g of azacytosine in 126 mL of acetonitrile. The mixture is brought to 50° C. and it is stirred for 90 minutes. 7 mL titanium tetrachloride and then a solution of 16.7 g of 1,2,3,5-tetra-O-acetyl-D-ribofuranose in 33 mL of acetonitrile are added to the limpid solution, in about ten minutes. Stirring is maintained for 120 minutes, it is cooled to room temperature and it is slowly poured onto a mixture constituted by 500 ml of dichloromethane and 330 mL of water into which 9.5 g of sodium bicarbonate had been previously dissolved. Stirring is carried out for 15 minutes and the pH is adjusted to pH=4.5 using 30% sodium hydroxide in water. It is filtered on earth filter, the mixture is left to settle and phases are separated. The aqueous phase is washed twice using 125 ml of dichloromethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 15 mL of a 10% solution of sodium methylate in methanol are added. It is stirred for 1 hour, it is cooled to room temperature, it is stirred to complete precipitation and the solid is filtered by washing it on the filter with methanol. 4.7 g of azacitidine with HPLC purity (UV 254 nm) of 97.2% are obtained after drying at low pressure.

Example 5

Preparation of Azacitidine 34.7 mL of BSTFA are added to a suspension of 6.3 g of azacytosine in 126 mL of acetonitrile. The mixture is brought to 50° C. and it is stirred for 90 minutes. 11.35 mL of trimethylsilyltriflate and then a suspension of 29.0 g of 1-O-acetyl-2,3,5-tri-O-benzoyl-D-ribofuranose in 50 mL of acetonitrile are added to the limpid solution, in about ten minutes. Stirring is maintained for 75 minutes, it is cooled to ambient temperature and it is slowly poured onto a mixture constituted by 500 ml of dichloromethane and 330 ml of water into which 9.5 g of sodium bicarbonate had been previously dissolved. Stirring is carried out for 15 minutes and the pH is adjusted to pH=4.5 using acetic acid. The mixture is left to settle and phases are separated. The aqueous phase is washed twice using 125 ml of dichloromethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 15 mL of a 10% solution of sodium methylate in methanol are added. It is stirred for 1 hour, it is cooled to ambient temperature, it is stirred to complete precipitation and the solid is filtered by washing it on the filter with methanol. 5.4 g of azacitidine with HPLC purity (UV 254 nm) of 94.1% are obtained after drying at low pressure.

Example 6

Preparation of Azacitidine 34.7 mL of BSTFA are added to a suspension of 6.3 g of azacytosine in 126 mL of dichloromethane. The mixture is brought to reflux temperature and it is stirred for 90 minutes. 11.35 mL of trimethylsilyltriflate and then a solution of 16.7 g of 1,2,3,5-tetra-O-acetyl-D-ribofuranose in 33 mL of dichloromethane are added to the limpid solution, in about ten minutes. Reflux and stirring are maintained for two hours, it is cooled to room temperature, 250 mL of methanol are added controlling the temperature in an ice bath. Concentration is carried out at low pressure until a residue volume of about 150 mL is obtained, 250 mL of methanol are added and once again concentration is carried out at low pressure until a residue volume of about 150 mL is obtained. 200 mL of methanol are added, it is heated to 50° C. and 48 mL of a 10% solution of sodium methylate in methanol are added. It is stirred for 1 hour, it is cooled to room temperature, it is stirred to complete precipitation and the solid is filtered by washing it on the filter with methanol.

9.9 g of azacitidine with HPLC purity (UV 254 nm) of 98.9% are obtained after drying at low pressure.

After recrystallisation from methanol-dimethyl sulfoxide the HPLC purity (UV 254 nm) is of 99.7%.

Example 7

Preparation of Azacitidine 34.7 mL of BSTFA are added to a suspension of 6.3 g of azacytosine in 126 mL of dichloromethane. The mixture is brought to reflux temperature and it is stirred for 90 minutes. 11.35 mL of trimethylsilyltriflate and then a solution of 29 g of 2,3,5-tri-O-benzoyl-1-O-acetyl-D-ribofuranose in 50 mL of dichloromethane are added to the limpid solution, in about ten minutes. Reflux and stirring are maintained for two hours, it is cooled to room temperature and the reaction mixture is poured onto 250 mL of methanol controlling the temperature in an ice bath. Concentration is carried out at low pressure until a residue volume of about 150 mL is obtained, 250 mL of methanol are added and once again concentration is carried out at low pressure until a residue volume of about 150 mL is obtained. 200 mL of methanol are added, it is heated to 50° C. and 48 mL of a 10% solution of sodium methylate in methanol are added. It is stirred for 1 hour, it is cooled to room temperature, it is stirred to complete precipitation and the solid is filtered by washing it on the filter with methanol.

9.3 g of azacitidine with HPLC purity (UV 254 nm) of 91.6% are obtained after drying at low pressure.

Example 8

Preparation of Azacitidine 34.7 mL of BSTFA are added to a suspension of 6.3 g of azacytosine in 126 mL of dichloroethane. The mixture is brought to reflux temperature and it is stirred for 90 minutes. 11.35 mL of trimethylsilyltriflate and then a solution of 16.7 g of 1,2,3,5-tetra-O-acetyl-D-ribofuranose in 50 mL of dichloroethane are added to the limpid solution, in about ten minutes. Reflux and stirring are maintained for 60 minutes, it is cooled to ambient temperature and it is poured on a solution of 9.5 g of sodium bicarbonate in 330 ml of water. It is stirred for ten minutes, the pH is adjusted to pH=4.5 using acetic acid. It is left to settle, phases are separated, the aqueous phase is washed twice using 125 ml of dichloroethane for each washing. The organic phases which are anhydrified by treating them with anhydrous calcium chloride are combined. Concentration is carried out at low pressure until a viscous residue is obtained. The residue is recovered with 250 mL of methanol, it is concentrated once again at low pressure until a viscous residue is obtained. 250 mL of methanol are added, it is heated to 50° C. and 10 mL of a 10% solution of sodium methylate in methanol are added. It is stirred for 1 hour, it is cooled to room temperature, it is stirred to complete precipitation and the solid is filtered by washing it on the filter with methanol.

5.0 g of azacitidine with HPLC purity (UV 254 nm) of 91.4% are obtained after drying at low pressure.

Example 9

Preparation of Decitabine 34 mL of BSTFA are added to a suspension of 6.4 g of azacytosine in 300 mL of acetonitrile. The mixture is brought to 50° C. and it is stirred for 90 minutes. It is cooled to ambient temperature, 6.3 mL of trimethylsilyltriflate and 11.1 g of 1-chloro-3,5-di-p-toluoyl-2-deoxy-D-ribofuranose are added to the solution, in about ten minutes. It is stirred for 140 minutes, 400 mL of methanol are added controlling the temperature in an ice bath. Concentration is carried out at low pressure until a viscous residue is obtained, 400 mL of methanol are added, it is heated to 50° C. and 36 mL of 30% solution of sodium methylate in methanol are added. It is stirred for 1 hour, it is cooled to 0° C., it is stirred to complete precipitation and the solid is filtered by washing it on the filter with methanol. 2.3 g of decitabine with HPLC purity (UV 254 nm) of 99.2% are obtained after drying at low pressure.

After recrystallisation from methanol the HPLC purity (UV 254 nm) is 99.8%.

The invention claimed is:

1. A process to synthesize azacitidine or decitabine, comprising
   a) reacting azacytosine with a silylating agent in acetonitrile, wherein said silylating agent is N,O-bis-trimethylsilyl-trifluoroacetamide and
   b) obtaining silylated azacytosine, wherein said silylated azacytosine is not isolated,
   c) reacting the silylated azacytosine with a derivative of D-ribofuranose having acylated hydroxyl functions wherein said reacting step occurs in acetonitrile of step a); and
   d) deprotecting the acylated intermediates.

2. The process according to claim 1, wherein 3 to 100 parts by volume of said acetonitrile are used for each part by weight of azacytosine.

3. The process according to claim 1, wherein 2 to 3 moles of N,O-bis-trimethylsilyl-trifluoroacetamide are used per mole of azacytosine.

4. The process according to claim 1, wherein said silylating reaction is performed at a temperature comprised between 0° C. and the reflux temperature of the reaction mixture.

5. The process according to claim 1, wherein said derivative is selected from the group consisting of 1,2,3,5-tetra-O-acetyl-D-ribofuranose and 1-O-acetyl-2,3,5-tri-O-benzoyl-D-ribofuranose.

6. The process to synthesize decitabine according to claim 1, in step c) further comprising reacting the silylated azacytosine with a derivative of 2-deoxy-D-ribofuranose having a leaving group in position 1 and the remaining hydroxyl functions acylated, obtaining acylated intermediates and deprotecting said acylated intermediates.

7. The process according to claim 6, wherein said leaving group is selected from the group consisting of: an alkoxy group, an acyloxy group and a halogen.

8. The process according to claim 6, wherein said acyl group is selected from the group consisting of: acetyl, p-toluoyl, p-chloro-benzoyl and p-nitro-benzoyl.

9. The process according to claim 6, wherein said derivative of 2-deoxy-D-ribofuranose is selected from the group consisting of: 1-chloro-3,5-di-p-toluoyl-2-deoxy-D-ribofuranose and 1-chloro-3,5-bis-p-chlorobenzoyl-2-deoxy-D-ribofuranose.

10. The process according to claim 6, wherein said reacting step is performed in the presence of a Lewis acid.

11. The process according to claim 10, wherein said Lewis acid is selected from the group consisting of: tin tetrachloride, titanium tetrachloride, zinc chloride, boron trifluoride etherate, trimethylsilyltriflate and trimethylsilylnonaflate.

12. The process according to claim 6, wherein said reaction is performed at a temperature comprised between 0° C. and the reflux temperature of the reaction mixture.

13. The process according to claim 6, wherein said deprotecting step is performed in a protic organic solvent.

14. The process according to claim 3, wherein from 2.2 to 2.5 moles of N,O-bis-trimethylsilyl-trifluoroacetamide are used per mole of azacytosine.

15. The process according to claim 7, wherein said leaving group is a methoxy group, an acetyloxy group or a chlorine atom.

16. The process according to claim 13, wherein said protic organic solvent is a $C_1$-$C_4$ alcohol.

17. The process according to claim 16, wherein said $C_1$-$C_4$ alcohol is methanol.

* * * * *